US009567633B2

(12) United States Patent
Gao et al.

(10) Patent No.: US 9,567,633 B2
(45) Date of Patent: Feb. 14, 2017

(54) METHOD FOR DETECTING HYDROXYLMETHYLATION MODIFICATION IN NUCLEIC ACID AND USE THEREOF

(71) Applicant: BGI TECH SOLUTIONS CO., LTD., Shenzhen (CN)

(72) Inventors: Fei Gao, Shenzhen (CN); Junwen Wang, Shenzhen (CN); Xiuqing Zhang, Shenzhen (CN); Huanming Yang, Shenzhen (CN)

(73) Assignee: BGI TECH SOLUTIONS CO., LTD. (CN)

( * ) Notice: Subject to any disclaimer, the term of this patent is extended or adjusted under 35 U.S.C. 154(b) by 99 days.

(21) Appl. No.: 14/360,594

(22) PCT Filed: Nov. 21, 2012

(86) PCT No.: PCT/CN2012/084964
§ 371 (c)(1),
(2) Date: Aug. 6, 2014

(87) PCT Pub. No.: WO2013/075629
PCT Pub. Date: May 30, 2013

(65) Prior Publication Data
US 2015/0031552 A1 Jan. 29, 2015

(30) Foreign Application Priority Data
Nov. 24, 2011 (CN) .......................... 2011 1 0376589

(51) Int. Cl.
*C12Q 1/68* (2006.01)
*C12Q 1/54* (2006.01)
(Continued)

(52) U.S. Cl.
CPC ............. *C12Q 1/6874* (2013.01); *C12Q 1/683* (2013.01); *C12Q 2600/154* (2013.01)

(58) Field of Classification Search
CPC ......... C12Q 1/68; C12Q 1/6874; C07H 21/02; C40B 30/04; G01N 33/52
(Continued)

(56) References Cited

FOREIGN PATENT DOCUMENTS

WO  WO 2011/025819  *  3/2011
WO  WO 2011/127136  *  10/2011

OTHER PUBLICATIONS

U.S. Appl. No. 14/360,594—SEQ ID No. 1 search results, printed on Oct. 23, 2015, p. 1.*
(Continued)

*Primary Examiner* — Narayan Bhat
(74) *Attorney, Agent, or Firm* — Alston & Bird LLP

(57) ABSTRACT

A method for detecting hydroxymethylation modification in nucleic acid comprises: glycosylating the nucleic acid, digesting with MspI, ligating the digested fragments to a biotin-labeled linker at both ends thereof, digesting with NlaIII; capturing the digested fragments using streptavidin magnetic beads to produce fragments having the biotin-labeled linker at one end and a CATG 4-base sticky end at the other end, wherein these fragments reveal modification information of their adjacent CCGG sites; ligating the CATG sticky end to a linker containing a recognition site of MmeI or Ecop15I, digesting with corresponding restriction endonuclease to produce short sequence fragments that can reveal modification information of their adjacent CCGG sites; and performing a tag number comparison to obtain information about methylation and hydroxymethylation modification relative levels. A use of the method is also provided.

15 Claims, 4 Drawing Sheets

(51) Int. Cl.
  *C12P 19/18*  (2006.01)
  *C12M 1/34*  (2006.01)
  *C12N 15/74*  (2006.01)
  *G01N 31/22*  (2006.01)
  *G01N 33/52*  (2006.01)
  *C07H 21/04*  (2006.01)
  *C40B 40/06*  (2006.01)

(58) Field of Classification Search
  USPC . 435/6.1, 6.11, 14, 97, 478, 287.2; 422/430; 536/23.1, 24–2; 506/16
  See application file for complete search history.

(56) References Cited

OTHER PUBLICATIONS

U.S. Appl. No. 14/360,594—SEQ ID No. 2 search results, printed on Oct. 23, 2015, p. 1.*
U.S. Appl. No. 14/360,594—SEQ ID No. 3 search results, printed on Oct. 23, 2015, p. 1.*
U.S. Appl. No. 14/360,594—SEQ ID No. 4 search results, printed on Oct. 23, 2015, p. 1.*
U.S. Appl. No. 14/360,594—SEQ ID No. 5 search results, printed on Oct. 23, 2015, p. 1.*
U.S. Appl. No. 14/360,594—SEQ ID No. 6 search results, printed on Oct. 23, 2015, p. 1.*
U.S. Appl. No. 14/360,594—SEQ ID No. 7 search results, printed on Oct. 23, 2015, p. 1.*
U.S. Appl. No. 14/360,594—SEQ ID No. 8 search results, printed on Oct. 23, 2015, p. 1.*
U.S. Appl. No. 14/360,594—SEQ ID No. 9 search results, printed on Oct. 28, 2015, p. 1.*
U.S. Appl. No. 14/360,594—SEQ ID No. 10 search results, printed on Oct. 28, 2015, p. 1.*
Gao et al, Integrated detection of both 5-mC and 5-hmC by high-throughput tag sequencing technology highlights methylation reprogramming of bivalent genes during cellular differentiation, 2013, Epigentics, 8, 421-430 (Post Art).*

* cited by examiner (a)

(b)

(c)

METHOD FOR DETECTING HYDROXYLMETHYLATION MODIFICATION IN NUCLEIC ACID AND USE THEREOF

REFERENCE TO A SEQUENCE LISTING

This application includes an electronic sequence listing in a file named 446596_SEQLST.TXT created on Feb. 3, 2016 and containing 3,612 bytes.

FIELD OF THE INVENTION

The present invention relates to the field of genetic engineering, and particularly to a method for detecting hydroxymethylation modification in nucleic acid and use thereof.

BACKGROUND OF THE INVENTION 5-hydroxymethylcytosine (5hmC) was first reported in cytosines of bacteriophage in 1952, and this kind of modification was also found in mammalian cells recently, for instance, neurons and embryonic stem cells of mouse. Over the last few years, a lot of researches have been done in revealing the possible role 5hmC plays in genome organization and stem cell differentiation, and TET protease family has been proved to be involved in oxidizing 5mC to 5hmC.

Though 5hmC modified base has found long before, there is no effective enzyme or chemical methods to specifically identify it and to detect its distribution in the genome. Methylation-dependent restriction endonucleases MspJI family or McrBC cannot distinguish 5mC from 5hmC, in addition, methylation-sensitive restriction endonucleases, such as MspI and HpaII, share a same behavior when reacting with both 5mC and 5hmC in most cases. Meanwhile, bisulfite sequencing analysis, which is regarded as a golden standard for DNA methylation analysis, still cannot effectively discriminate between 5mC and 5hmC. With the development of 5hmC specific antibodies, immunology-based 5hmC detecting methods, for example, dot blotting analysis, immunofluorescence and immunohistochemistry have been applied to the researches regarding hydroxymethylation modification. However, these methods, which are able to detect 5hmC's existence and expression level in a cell or a tissue, still cannot locate 5hmC's genome-wide distributions. By far, the main strategy for detecting genome-wide distribution patterns of 5hmC comprises the steps of enrichment, capturing and sequencing, for example, hMeDIP, anti-CMS and JBP-pull down, such methods comprising the enrichment-capturing step still cannot obtain the distribution of 5hmC at a single-base resolution level, meanwhile, such antibody/protein-dependent methods are also restricted because of non-specific capture or capture bias.

As discussed above, a large-scale detection technique for detecting accurate distributions of 5hmC in DNA is required, and a method for accurately detecting hydroxymethylation modification is urgently needed. This method will be an important tool in the researches about genome-wide distribution of 5hmC and relevant epigenetic regulation mechanisms, furthermore, this method will be a useful tool in studying the roles of 5hmC in disease occurrence and individual development.

SUMMARY OF THE INVENTION

An object of this invention is to provide a method for detecting hydroxymethylation modification in nucleic acid. Another object of the present invention is to provide a use of this method.

In a first aspect of this invention, the present invention provides a method of detecting hydroxymethylation modification in nucleic acid, comprising:

(1) glycosylating the nucleic acid to obtain a glycosylated nucleic acid having glycosylated hydroxymethylated bases derived from hydroxymethylated bases;

(2) respectively digesting a control nucleic acid that is unglycosylated and the glycosylated nucleic acid obtained from the step (1) by using a first restriction endonuclease to produce first control nucleic acid fragments and sample nucleic acid fragments; digesting the control nucleic acid or the glycosylated nucleic acid by using a second restriction endonuclease to produce second control nucleic acid fragments;

(3) respectively ligating the first control nucleic acid fragments, the sample nucleic acid fragments and the second control nucleic acid fragments that are obtained from the step (2) to a biotin-labeled linker to produce a first control ligated product, a sample ligated product and a second control ligated product with each ligated product having the biotin-labeled linker;

(4) respectively digesting the first control ligated product, the sample ligated product and the second control ligated product that are obtained from the step (3) with NlaIII restriction endonuclease to produce a first control NlaIII digested product, a sample NlaIII digested product and a second control NlaIII digested product, with each NlaIII digested product having the biotin-labeled linker at one end and a sticky end at the other end;

(5) respectively linking the first control NlaIII digested product, the sample NlaIII digested product and the second control NlaIII digested product that are obtained from the step (4) to a second linker having a recognition site of a specific restriction endonuclease; then obtaining a first control secondary-ligated product, a sample secondary-ligated product and a second control secondary-ligated product;

(6) respectively digesting the first control secondary-ligated product, the sample secondary-ligated product and the second control secondary-ligated product that are obtained from the step (5) with the specific restriction endonuclease to produce a first control final digested product, a sample final digested product and a second control final digested product, with each final digested product having the second linker at one end and a sticky end at the other end;

(7) ligating the first control final digested product, the sample final digested product and the second control final digested product that are obtained from the step (6) to a sequencing adaptor, then amplifying the sequencing adaptor-ligated products to produce a first control sequencing library, a sample sequencing library and a second control sequencing library; and (8) sequencing all the libraries obtained from the step (7), analyzing and comparing sequence information to obtain information about hydroxymethylation modification in the nucleic acid.

In a preferred embodiment of the present invention, the nucleic acid in the step (1) is genomic DNA.

In a preferred embodiment of the present invention, the nucleic acid in the step (1) is obtained from animals, plants, bacteria, fungi, virus, or a combination thereof.

In a preferred embodiment of the present invention, the glycosylation treatment in the step (1) is achieved by transferring a glucose moiety from a substrate uridine diphosphoglucose to 5-hydroxymethylcytosine (5-hmC) with an enzyme T4-BGT, thereby generating β-glucosyl-5-hydroxymethylcytosine (5-gmC).

In a preferred embodiment of the present invention, the first restriction endonuclease used in the step (2) is MspI.

In a preferred embodiment of the present invention, the second restriction endonuclease used in the step (2) is HpaII.

In a preferred embodiment of the present invention, the sequences of the biotin-labeled linker are SEQ ID NO: 1 and SEQ ID NO: 2.

In a preferred embodiment of the present invention, the step (4) further comprises a step of: capturing fragments produced from the NlaIII digestion by using streptavidin magnetic beads to obtain the first control NlaIII digested product, the sample NlaIII digested product and the second control NlaIII digested product, with each NlaIII digested product having the biotin-labeled linker at one end and the sticky end at the other end.

In a preferred embodiment of the present invention, the second linker used in the step (5) is composed of two paired oligonucleotides, and sequences of the two oligonucleotides are SEQ ID NO: 3 and SEQ ID NO: 4; or alternatively, the sequences of the two oligonucleotides are SEQ ID NO: 5 and SEQ ID NO: 6; or alternatively, the sequences of the two oligonucleotides are SEQ ID NO: 7 and SEQ ID NO: 8.

In a preferred embodiment of the present invention, the specific restriction endonuclease used in the step (6) is MmeI or Ecop15I.

In a preferred embodiment of the present invention, the specific restriction endonuclease used in the step (6) is MmeI, and the obtained digested products with a length of 20 bp have the second linker at one end and the sticky end at the other end.

In a preferred embodiment of the present invention, the specific restriction endonuclease used in the step (6) is Ecop15I, and the obtained digested products with a length of 25 bp have the second linker at one end and the sticky end at the other end.

In a preferred embodiment of the present invention, the sequencing adaptor used in the step (7) is composed of two paired oligonucleotides, and sequences of the two oligonucleotides are SEQ ID NO: 9 and SEQ ID NO: 10.

In a preferred embodiment of the present invention, the sequencing step in the step (8) is performed by using a sequencing platform selected from the group consisting of: Illumina Solaxa, Roche 454, ABI SOLID, Helicos TRUE Single-Molecule Sequencing System, PacBio Single-Molecule Real-Time Sequencing System, Oxford Nanopore Single-Molecule Sequencing System.

In a preferred embodiment of the present invention, the analysis and comparison of sequence information in the step (8) comprise the following steps of:
  (i) filtering raw reads of each library after sequencing to obtain high-quality reads; performing an in-silico digestion of a reference sequence to produce a virtual library consisting of theoretical digested fragments;
  (ii) performing an alignment of the high-quality reads with DNA sequences from the virtual library that are both obtained from the step (i); normalizing statistical data produced from the alignment to obtain normalized data of sequencing depths from the three libraries;
  (iii) calculating both methylation level and hydroxymethylation level of each CCGG site according to the normalized data obtained from the step (ii); and
  (iv) performing statistical analyses on the methylation and hydroxymethylation profiles of all CCGG sites in the sample and on the distributions of methylation and hydroxymethylation levels in different chromatins, based on the methylation level and the hydroxymethylation level of each CCGG site obtained from the step (iii).

In a second aspect of this invention, the present invention provides a kit for accurately detecting hydroxymethylation modification in genome, comprising the following components:
  (1) a first container and a reagent therein for glycosylation modification;
  (2) a second container and a reagent therein for restriction endonuclease digestion;
    wherein in a preferred embodiment of the present invention, the restriction endonuclease in the second container comprises MspI, HpaII, MmeI and NlaIII;
    wherein in a preferred embodiment of the present invention, the restriction endonuclease in the second container comprises MspI, HpaII, Ecop15I and NlaIII;
  (3) a third container and a biotin-labeled linker therein, wherein the biotin-labeled linker is composed of two paired oligonucleotides, and sequences of the two oligonucleotides are SEQ ID NO: 1 and SEQ ID NO: 2;
  (4) a fourth container and a second linker therein, wherein the second linker is composed of two paired oligonucleotides, and sequences of the two oligonucleotides are SEQ ID NO: 3 and SEQ ID NO: 4; or alternatively, the sequences of the two oligonucleotides are SEQ ID NO: 5 and SEQ ID NO: 6; or alternatively, the sequences of the two oligonucleotides are SEQ ID NO: 7 and SEQ ID NO: 8;
  (5) a fifth container and a sequencing adaptor therein, wherein the sequencing adaptor is composed of two paired oligonucleotides, and sequences of the two oligonucleotides are SEQ ID NO: 9 and SEQ ID NO: 10.

In a preferred embodiment of the present invention, the kit further comprises a reagent for magnetic bead-based capturing, a reagent for nucleic acid purification, or a combination thereof.

It should be understood that, within the scope of the present invention, the technical features mentioned above and the detailed technical features discussed below can be combined to form new technical solutions or preferred technical solutions. Here we will not go into details of them because of the limitation of space.

BRIEF DESCRIPTION OF THE DRAWINGS

Various preferred embodiments will now be described with reference to the figures.

FIG. 2(a) shows a size distribution of the fragments in the library generated from T4-BGT glycosylation and subsequent MspI digestion of stem cells h9 genomic DNA; FIG. 2(b) shows a size distribution of the fragments in the library generated from direct MspI digestion of stem cells h9 genomic DNA; and FIG. 2(c) shows a size distribution of the fragments in the library generated from direct HpaII digestion of stem cells h9 genomic DNA.

DETAILED DESCRIPTION OF ILLUSTRATED EMBODIMENTS

Figure 1:
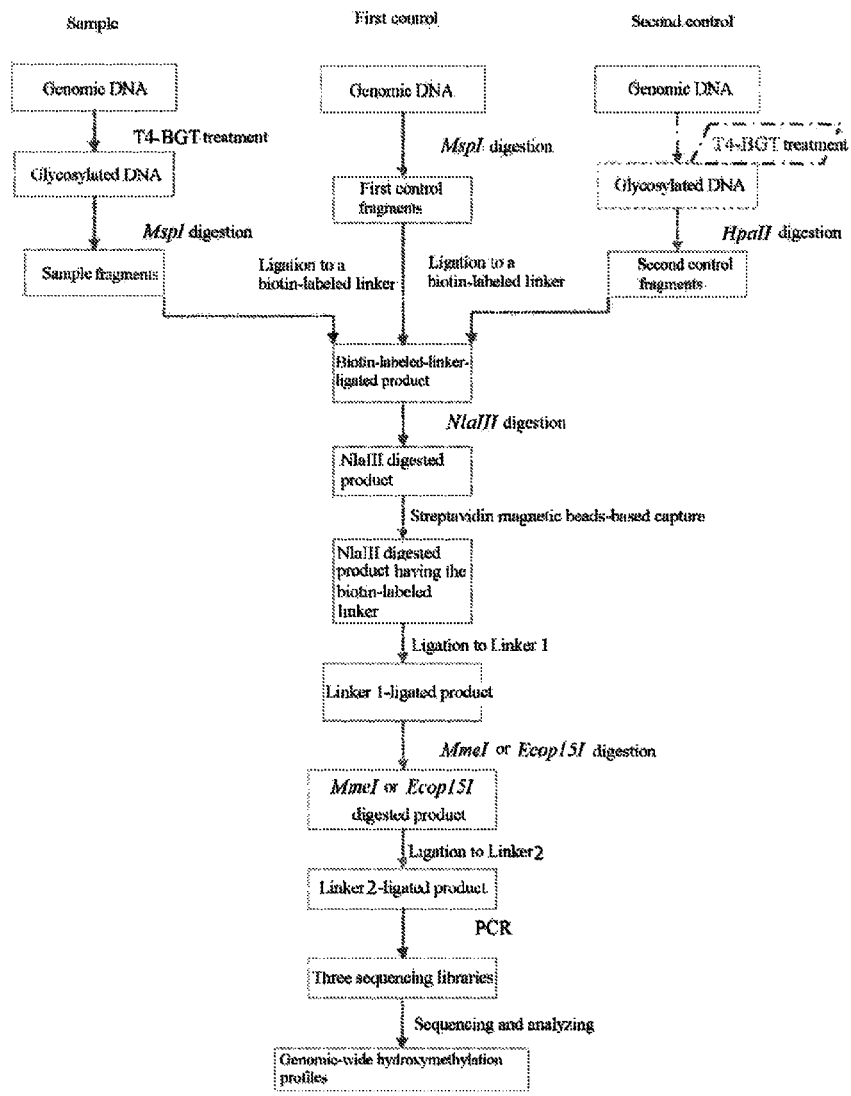
FIG. 1 shows a method for detecting hydroxymethylation modification in a preferred embodiment of the present invention.

After extensive research, a method for detecting methylation and hydroxymethylation in nucleic acid is developed for the first time, specifically, the method comprises the following steps of: glycosylating the nucleic acid, digesting with MspI, ligating the digested fragments to a biotin-labeled linker at both ends thereof, digesting with NlaIII; capturing the digested fragments using streptavidin magnetic beads to produce fragments having the biotin-labeled linker at one end and a CATG 4-base sticky end at the other end, wherein these fragments reveal modification information of their adjacent CCGG sites; ligating the CATG sticky end to a linker containing a recognition site of MmeI or Ecop15I, digesting with corresponding restriction endonuclease to produce short sequence fragments that can reveal modification information of their adjacent CCGG sites; and performing a tag number comparison to obtain information about methylation and hydroxymethylation modification relative levels.

DEFINITIONS

The term "comprising" as used herein may include "comprising", "substantially composed of . . . " and "composed of . . . ". The terms "more than a number" and "lower than a number" as used herein may include the number itself, for example, "more than 80%" means "≥80%", "lower than 2%" means "≤2%".

5-Hydroxymethylcytosine (5hmC)

5-hydroxymethylcytosine (5hmC) is a modified base in various cell types in mammals. 5hmC is generated through oxidation of 5-methylcytosine (5mC) by enzyme members of the TET enzyme family. The UV adsorption and chromatogram behaviors of 5hmC are similar to that of cytosine. 5-hydroxymethylcytosine (5hmC) presents at low levels in diverse cell types in mammals.

5hmC content is different at genome, cell or tissue level, immunoassay test shows that the percentage of 5-hmC measured is high in brain, liver, kidney and colorectal tissues (0.40-0.65%), while it is relatively low in lung (0.18%) and very low in heart, breast, and placenta (0.05-0.06%). Abundance of 5-hmC in the cancerous colorectal tissues was significantly reduced (0.02-0.06%) compared to that in normal colorectal tissues (0.46-0.57%). Strong enrichment of 5hmC is found within exons and near transcriptional start sites. 5hmC was especially enriched at the start sites of genes whose promoters bear dual histone 3 lysine 27 trimethylation (H3K27me3) and histone 3 lysine 4 trimethylation (H3K4me3) marks. It is reported that 5hmC has a probable role in transcriptional regulation.

T4 Phage β-Glucosyltransferase (T4-BGT)

T4 phage β-glucosyltransferase can efficiently transfer a glucose moiety of uridine diphosphoglucose (UDP-Glucose) to 5-hydroxymethylcytosine (5hmC) residue in double-stranded DNA, thereby generating β-glucosyl-5-hydroxymethylcytosine (5 gmC), 5 gmC cannot be cleaved by MspI. Hence, after a genome has been glycosylated by T4-BGT, hydroxymethylation modification of a specific single CCGG site can be semi-quantitatively detected using PCR or quantitatively detected using Q-PCR.

Primer

The term "primer" as used herein refers to an oligonucleotide that is characterized by an ability to be extended against a template oligonucleotide, so that an oligonucleotide whose sequence is complementary to that of at least a portion of the template molecule is linked to the primer. A primer may be natural RNA or DNA, it may also be non-natural nucleotides such as LNA or ZNA for example. A primer is substantially complementary to at least a specific portion of the sequence of the template. A primer has to be fully complementary to a portion of the sequence of the template so as to start the extension, but this does not mean the primer has to be completely complementary to the portion. For example, a primer has 3'-terminal nucleotides being complementary to a template and has 5'-terminal nucleotides being uncomplimentary to the template, this kind of primer is still substantially complementary to the template. A primer that is incompletely-complementary to the template will form a primer-template complex and start the extension, provided that the primer has a long enough sequence to combine with the template.

High-Throughput Sequencing

"Re-sequencing" of genome makes it possible to find abnormal changes of genes that are relative to various kinds of diseases as early as possible, which helps to diagnose and treat diseases in an individual. Various second-generation sequencing platforms can be selected, such as 454 FLX (Roche), Solexa Genome Analyzer (Illuminutesa) and SOLID (Biosystems). Compared with traditional 96-capillary DNA Analyzers, the advantages of these platforms are high-throughput, which produce up to 400 thousands to 4 million reads and 1 G to 14 G bases in a single run due to the read length from 25 bp to 450 bp in different platforms. Taking Solexa high-throughput sequencing as an example, there are the two main steps for the sequencing: the generation of DNA-cluster and subsequent automated sequencing. First, a mixture of PCR amplification products is hybridized with sequencing probes immobilized on a solid-phase carrier, then a solid-phase bridge amplification is initiated, and the cluster is generated. Second, the clusters are sequenced using Sequencing-by-Synthesis (SBS) technology, consequently the sequence of disease-related nucleic acid will be obtained.

The DNA-cluster is formed by using a flow cell. The ends of the DNA fragments are ligated to two unique adapters. The flow cell surface is coated with single stranded primers that correspond to the sequences of the adapters ligated, Single-stranded adapter-ligated fragments are thus bound to the surface of the flow cell exposed to reagents for extension. The bound single-stranded DNA becomes double-stranded after amplification, and then converted to single-stranded DNA after denaturation, the single-stranded DNA has one end immobilized on the flow cell and the other end randomly bonds to an adjacent complementary primer, which forms a "bridge". Millions of bridged single-stranded DNA fragments will be presented on the flow cell surface, the primer on the surface then serves as a starting point for DNA synthesis, thereby generating double-stranded DNA. These double-stranded DNA are converted to single strands during denaturation, and then bridged again as templates for the next amplification reaction. After 30 cycles, 1000-fold amplification will be yielded, which may also be referred to as monoclonal DNA-cluster.

Sequencing-by-Synthesis (SBS) technology is used for sequencing the DNA cluster. SBS technology uses a proprietary reversible terminator-based method that detects single bases as they are incorporated into growing DNA strands. A fluorescently-labeled terminator is imaged as each dNTP is added and then cleaved to allow incorporation of the next base, thus accurate sequence of bases can be obtained by a plurality of cycles. Indexes (or "barcodes") may be used in Solexa multiplexed sequencing to distinguish different samples. After routine sequencing, additional seven cycles are required for the index part. Using the index, up to 12 different samples can be distinguished in one channel.

Detecting Method

This invention provides a method for accurately detecting hydroxymethylation modification sites. In a preferable embodiment of the present invention, the method comprises the following steps (also shown in FIG. 1).

1. Glycosylation modification of 5hmC in genomic DNA: intact genomic DNA that is not polluted by protein or RNA is glycosylated by using T4 Phage β-glucosyltransferase (T4-BGT); at the same time, a same amount of the genomic DNA is prepared as a control group without the glycosylation modification.

As for the glycosylated group, a glucose moiety from a substrate uridine diphosphoglucose (UDP-Glucose) is transferred to 5-hydroxymethylcytosine (5hmC) of double-stranded DNA with an enzyme T4-BGT, thereby generating β-glucosyl-5-hydroxymethylcytosine (5 gmC). The reaction is sequence-independent, such that all 5hmC will be glycosylated, however, unmodified cytosine and methylated 5mC will not be glycosylated; the control group without the adding of T4-BGT will not be glycosylated.

In the method of the present invention, the genomic DNA may extracted from animal tissues, cells or other sources, provided that there exits $C^hCGG$ hydroxymethylation modification in CCGG sites of the genomic DNA. Therefore, the detecting method of the present invention can be widely used.

2. Digestion with restriction endonuclease: DNA in the glycosylated group and the control group are both digested with MspI; at the same time, intact genomic DNA that is not polluted by protein or RNA is digested with an enzyme HpaII.

MspI and HpaII have different sensitivity to methylation, HspII only recognizes and cleaves unmodified CCGG sites; MspI recognizes and cleaves all kinds of modified CCGG sites including CCGG, $C^mCGG$ and $C^hCGG$, but not $C^gCGG$; wherein the superscript "m" in the DNA sequence of the present invention refers to "methylation", while "h" refers to "hydroxymethylation". Hence, the ends of the digested DNA fragments in different groups may contain different modification information. Specifically, the ends of the DNA fragments generated from glycosylation and subsequent MspI digestion contain CCGG and $C^mCGG$ information in the genomic DNA; the ends of the DNA fragments generated from direct HpaII digestion only contain CCGG information in the genomic DNA; and the ends of the DNA fragments generated from direct MspI digestion contain CCGG, $C^mCGG$ and $C^hCGG$ information in the genomic DNA.

3. Ligation to Biotin-labeled linker: in each of the groups, two ends of the digested DNA fragment are ligated to a biotin-labeled linker using DNA ligase.

4. Digestion with NlaIII: in each of the groups, the DNA fragments having the biotin-labeled linker at two ends thereof are digested with restriction endonuclease NlaIII which cleaves the DNA fragments at a specific "CATG" site, thereby producing fragments having the biotin-labeled linker at one end and a sticky end with CATG 4-base overhang at the other end, and together with some fragments with sticky ends at both ends.

5. Streptavidin magnetic beads-based capture: the DNA fragments having the biotin-labeled linker at one end and the sticky end CATG at the other end are captured by magnetic beads coupling with M-280 streptavidin, then some fragments with sticky ends at both ends are washed and removed, which will not affect subsequent analyses.

6. Ligation to Linker N: the DNA fragments that have been captured by streptavidin magnetic beads are ligated to a linker N contains a MmeI restriction endonuclease recognition site therein by using DNA ligase, thereby, one end of the generated DNA fragments is coupled to the magnetic bead through the affinity between the biotin and the streptavidin, while the other end of the generated DNA fragments is ligated to the linker N which has the MmeI recognition site therein. The recognition site of MmeI is 5'TCCRAC3', wherein the R is base A or G. In another preferred embodiment of the present invention, in the linker N, the MmeI restriction endonuclease recognition site can be replaced with Ecop15I restriction endonuclease recognition site.

7. Digestion with MmeI or Ecop15I: the generated DNA fragments are digested with MmeI which recognizes the digestion site in the Linker N to generate 20 bp insertion fragments and corresponding disposable fragments linked to the magnetic beads. Wherein one end of the insertion fragment is ligated to the Linker N, and the other end of the insertion fragment is a sticky end with two arbitrarily protruded bases. Each insertion fragment ligated to the Linker N represents the modification information of its adjacent CCGG sites. In another preferred embodiment of the present invention, the generated DNA fragments are digested with Ecop15I which recognizes the digestion site in the Linker N to generate 25 bp insertion fragments and corresponding fragments linked to the magnetic beads. Wherein one end of the insertion fragment is ligated to the Linker N, and the other end of the insertion fragment is a sticky end with two arbitrarily protruded bases. Each insertion fragment ligated to the Linker N represents the modification information of its adjacent CCGG sites.

8. Ligation to P7 adaptor: supernatants (containing DNA fragments ligated to the Linker N) of the MmeI or Ecop15I digested products are purified, then P7 adaptor is ligated to the DNA fragments by using DNA ligase, the ligated product is then purified.

9. PCR amplification and purification: PCR is performed using linker N and P7 adaptor sequences as primers, the amplified products are purified with 6% native-PAGE, Agilent 2100 is used to determine fragment size of the purified products, Q-PCR was used to accurately quantify of the purified products, then the products are sequenced on Hiseq2000 sequencer.

10. Sequencing and data analysis: After testing, the qualified library was sequenced on HiSeq 2000 sequencer with single-end reads of 50 bp. The sequencing data was normalized, the amount of 20 bp short sequence DNA corresponding to each CCGG site was compared among the three different libraries. Thus, the information about methylation level and hydroxymethylation level of each CCGG site is obtained.

In a preferred embodiment of the present invention, analysis and comparison of sequence information comprise the following steps of: (i) filtering raw reads of each library after sequencing to obtain high-quality reads; performing an in-silico digestion of a reference sequence to produce a virtual library consisting of theoretical digested fragments; (ii) performing an alignment of the high-quality reads with DNA sequences from the virtual library that are both obtained from the step (i); normalizing statistical data produced from the alignment to obtain normalized data of sequencing depths from the three libraries; (iii) calculating both methylation level and hydroxymethylation level of each CCGG site according to the normalized data obtained from the step (ii); and (iv) performing statistical analyses on the methylation and hydroxymethylation profiles of all CCGG sites in the sample and on the distributions of methylation and hydroxymethylation levels in different chromatins, based on the methylation level and the hydroxymethylation level of each CCGG site obtained from the step (iii).

The filtering step in the step (i) comprises: removing sequence information of the sequencing adaptor from the raw reads of the library; removing reads that have N base number occupying more than 10% of total base number from the raw reads of the library; and removing reads in which the number of bases having quality value lower than 20 is more than 10% of total base number from the raw reads of the library.

The normalization in the step (ii) comprises the steps of: ranking the sequencing depths of CCGG sites in each library to obtain a ranking index of each CCGG site in each library; obtaining a ranking index of each CCGG site in each column, calculating a square deviation of three ranking indexes for each CCGG site, eliminating a site having a higher square deviation by cycling the ranking for n times, using the rest of m sites as a baseline for the normalization, wherein both m and n are positive integers; and normalizing the three libraries according to relative scales of the total amount of sequencing depths of the robust m remaining sites. In a preferred embodiment of the present invention, m ranges from 5000 to 15000, and n≥4.

Kit

This invention also provides a kit for accurately detection of genome-wide hydroxymethylation modification, comprising the following components:

(1) a first container and a reagent therein for glycosylation modification;

(2) a second container and a reagent therein for restriction endonuclease digestion;

in a preferred embodiment of the present invention, the restriction endonuclease reagent comprises MspI, HpaII, MmeI and NlaIII; optionally, the restriction endonuclease reagent comprises MspI, HpaII, Ecop15I and NlaIII;

(3) a third container and a biotin-labeled linker therein, preferably, the biotin-labeled linker is composed of two paired oligonucleotides, sequences of the two oligonucleotides are SEQ ID NO: 1 and SEQ ID NO: 2, for example;

(4) a fourth container and a second linker therein, wherein the second linker is composed of two paired oligonucleotides, preferably, nucleotide sequences of the two oligonucleotides are SEQ ID NO:3 and SEQ ID NO:4, optionally, the two oligonucleotides are SEQ ID NO:5 and SEQ ID NO:6, or SEQ ID NO:7 and SEQ ID NO:8.

(5) a fifth container and a sequence adaptor therein, preferably, the sequencing adaptor is composed of two paired oligonucleotides, for example, nucleotide sequences of the two oligonucleotides are SEQ ID NO: 9 and SEQ ID NO: 10.

In another preferred embodiment, the kit further comprises a reagent for streptavidin magnetic beads capturing, a reagent for nucleic acid purification, or a combination thereof.

Advantages of the Present Invention (1) This invention provides a method for genome-wide detecting of hydroxymethylation modification at single-base resolution with the help of high-throughput sequencing, and enables simultaneous detection of methylation modification of certain CCGG sites at single-base resolution.

(2) The amount of the detected sites obtained by using the method of the present invention is much more than that by existing method, therefore, the method of the present invention has an improved coverage on whole genome wide.

(3) The method of the present invention employs sequence tags to indirectly reflect modification status of each CCGG site, such that, only single-end sequencing is required. So the size of sequencing data as well as the cost will be greatly reduced.

Examples described below are merely specific embodiments of the present invention, but are not intended to limit the protection scope of the present invention. Detailed experimental procedures and conditions may not be included in the Examples, but these detailed experimental procedures and conditions have been described by Sambrook et al. in "Molecular cloning: a laboratory manual" (New York: Cold Spring Harbor Laboratory Press, 1989), or have been advised by the manufactures of the following reagents or instruments.

Main Instruments and Reagents

Main instruments used in the embodiments are listed in Table 1.

TABLE 1

| Name | Type | Manufacture |
|---|---|---|
| Instrument for PCR | Veriti Thermal Cycler | ABI |
| Agilent 2100 | 2100 Bioanalyzer | Agilent |
| NanoDrop 1000 (DNA concentration detector) | Spectrophotometer | Thermo Fisher Scientific |
| Gel Imaging System | Tanon | Tanon |
| Dark Reader Transilluminators | D195M | Clare Chemical Research |
| Thermomixer | Thermomixer comfort | Eppendorf |
| Refrigerated centrifuge | 5417R | Eppendorf |
| Desk centrifuge | 5418 | Eppendorf |
| Desk centrifuge | SVC-75004334 | Heraeus |
| Vertical mixer | HS3 | |
| Vertical electrophoresis system | Mini-PROTEAN Tetra cell | |
| Thermomixer | Comfort5355 | |
| Vortex mixer | QL-901 | |
| Magnet | 123-21D | Invitrogen |
| Electronic analytical balance | BS124S | Sartorius |

Main reagents used in the embodiments are listed in Table 2.

TABLE 2

| Name | Type | Manufacture |
|---|---|---|
| T4-BGT (T4 Phage β-glucosyltransferase) 25 × UDP-Glucose | M0357L | NEB |
| MspI | R0106M | |
| HpaII | R0171M | |
| T4 DNA ligase | M0202L | |
| NlaIII | R0125L | |
| MmeI | R0637L | |
| Phusion high fidelity DNA polymerase | M0530S | |
| 50 bp DNA Ladder | N3236L | |
| 50 bp ladder marker | MD108-01 | TIANGEN |
| T4 DNA Ligase (250U) | 15224-041 | Invitrogen |
| DL2000 marker | MD114-02 | TIANGEN |
| DynabeadsM -280 Streptavidin | 112.06D | Invitrogen |
| λ-HindIII marker | D3403A | TaKaRa |
| Biotin-linker | | |
| Linker N | | |
| P7 adaptor | | |
| P5 primer | | |
| P7 primer | | |
| Glycogen | AM9510 | Ambion |
| Phenol/chloroform/isoamylalcohol (25:24:1) | 15593-031 | Invitrogen |
| 3M NaoAc | 567422 | Calbiochem |

TABLE 2-continued

| Name | Type | Manufacture |
|---|---|---|
| 100% ethanol | | Made in China |
| 10 × TBE | AM9863 | Ambion |
| EDTA | 0322-500 g | Sangon Biotech |
| Spin-X Cellulose Acetate Filter (2 ml, 0.45 μm) | 8162 | Corning |
| NEB Buffer 2 | B7002S | NEB |
| Acryl/Bis solution (19:1) 40% (w/v) | SD6012 | Sangon Biotech |

Sequences of linker, adaptor and primer in the embodiments are listed in Table 3.

TABLE 3

| SEQ ID NO. | Name | Sequence |
|---|---|---|
| 1 | Biotin linker | 5'-Biotin-TTTGCAGAGGTTCGTAATCGAGTTGGGTGG-3' |
| 2 | | 3'-CGTCTCCAAGCATTAGCTCAACCCACCGC-5' |
| 3 | Linker | 5'-ACAGGTTCAGAGTTCTACAGTCCRACCATG-3' R = A or G |
| 4 | N | 5'GTYGGACTGTAGAACTCTGAAC-3' Y = C or T |
| 5 | | 5'-ACAGGTTCAGAGTTCTACAGTCCGACAGCAGCATG-3' |
| 6 | | 5'-CTGCTGTCGGACTGTAGAACTCTGAAC-3' |
| 7 | | 5'-ACAGGTTCAGAGTTCTACAGCAGCAGCATG-3' |
| 8 | | 5'-CTGCTGCTGTAGAACTCTGAAC-3' |
| 9 | P7 | 5'-TCGTATGCCGTCTTCTGCTTG-3' |
| 10 | adaptor | 3'-NNAGCATACGGCAGAAGACGAAC-5' |
| 11 | P5 primer | 5'-AATGATACGGCGACCACCGACAGGTTCAGAGTTCTACAGTCCGA-3' |
| 12 | P7 primer | 5'-CAAGCAGAAGACGGCATACGA-3' |

SEQ ID NO:3 and SEQ ID NO:4 are both linker N sequences having MmeII recognition site.

SEQ ID NO:5 and SEQ ID NO:6, as well as SEQ ID NO:7 and SEQ ID NO:8 are linker N sequences having Ecop15I recognition site.

Example 1

Glycosylation Modification of Genomic DNA

Material: h9 Cell Line

For both glycosylation treatment group and first control group, 1 μg of h9 cell line genomic DNA was used, a reaction system containing the following components in Table 4 was added in a 1.5 ml centrifuge tube.

TABLE 4

| Component | Glycosylation treatment group | First control group |
|---|---|---|
| h9 genomic DNA | 1 μg | 1 μg |
| 25 × UDP-Glucose | 4 μl | 4 μl |
| 10 × NEB buffer4 | 10 μl | 10 μl |
| T4-BGT | 30 units | 30 units (inactivated) |
| RNase-free water | up to 100 μl | up to 100 μl |

The reaction system was well mixed, centrifuged, and then incubated in a water bath at 37° C. for 16 hours, after the reaction, DNA was precipitated with ethanol and the ethanol precipitate was dissolve in 30 μl EB buffer.

Example 2

Restriction Endonuclease Digestion with MspI

DNA yielded from the glycosylation treatment group and the first control group was digested with restriction endonuclease MspI.

A reaction system containing the following components in Table 5 was added in a 1.5 ml centrifuge tube.

TABLE 5

| Component | Glycosylation treatment group | First control group |
|---|---|---|
| Purified DNA | 30 μl | 30 μl |
| 10 × NEB buffer4 | 10 μl | 10 μl |
| MspI | 500 units | 500 units |
| RNase-free water | up to 50 μl | up to 50 μl |

The reaction system was incubated in a water bath at 37° C. for 16-19 hours, the enzyme in the product was inactivated by heating at 80° C. for 20 minutes.

Example 3

Restriction Endonuclease Digestion with HpaII

An additional 1 μg of h9 cell line genomic DNA was directly digested with enzyme HpaII. A reaction system containing the following components in Table 6 was added in a 1.5 ml centrifuge tube.

TABLE 6

| Component | HpaII digestion group |
|---|---|
| h9 genomic DNA | 1 μg |
| 10 × NEB buffer4 | 10 μl |
| HpaII | 500 units |
| RNase-free water | up to 50 μl |

The reaction system was incubated in a water bath at 37° C. for 16-19 hours, the enzyme in the product was inactivated by heating at 80° C. for 20 minutes.

Example 4

Ligation of the Restriction Enzyme-Digested Product to a Biotin-Labeled Linker A reaction system containing the restriction enzyme-digested DNA and other components shown in Table 7 was added in a 1.5 ml centrifuge tube.

TABLE 7

| | |
|---|---|
| Digested DNA | 100 μl |
| Biotin-labeled linker (10 μM) | 3 μl |
| ATP (10 mM) | 12 μl |
| T4 DNA ligase (NEB) | 2 μl |

The reaction system was incubated at 16° C. for 5 hours. After the reaction, the ligated product was precipitated and purified with ethanol and the ethanol precipitate was dissolve in 172 μl of LoTE (3 mmol/L Tris-HCl, pH 7.5, 0.12 mmol/L EDTA).

Example 5

Digestion with NlaIII (NEB)

The biotin-labeled-linker-ligated product yielded from the Example 4 was used as a component of a reaction system shown in Table 8.

TABLE 8

| | |
|---|---|
| DNA | 172 μl |
| 100 × BSA | 2 μl |
| 10 × NEB buffer4 | 20 μl |
| NlaIII | 6 μl |
| TOTAL Volume | 200 μl |

The reaction system was incubated at 37° C. for 1 hour. After the reaction had been completed, 400 μl of Wash buffer D (Invitrogen) was added to the reaction system.

Example 6

Capture of Biotin-Labeled-Linker-Ligated DNA with Streptavidin Magnetic Beads 1. Preparation of Streptavidin Magnetic Beads
(1) Resuspend M-280 streptavidin magnetic beads, aspirate 200 μl of the resuspended M-280 streptavidin magnetic beads into a 1.5 ml Eppendorf tube (EP tube), place the EP tube on a magnet for 1 minute, and carefully remove the supernatant.
(2) Add 400 μl of Wash buffer D to the EP tube, resuspend the beads, place the EP tube on a magnet for 2 minutes, and carefully remove the supernatant;

2. Capture of Biotin-Labeled-Linker-Ligated DNA with Streptavidin Magnetic Beads after NlaIII Digestion
(1) Add a mixture of 200 μl of reaction solution of NlaIII digested DNA and 400 μl of Wash buffer D to the prepared beads, resuspend, incubate at room temperature for 20 minutes, shake the beads gently every 5 minutes during the incubation to prevent precipitation.
(2) Place the EP tube on a magnet for 2 minutes and remove the supernatant; then wash twice with 600 μl of Wash buffer D.
(3) Add 300 μl of 1× ligation buffer (Invitrogen) to each tube, resuspend, place the EP tube on a magnet for 1 minute and then remove the supernatant.

Example 7

Ligation with Linker N (1) Add reagents listed in Table 9 to the product captured by the beads.

TABLE 9

| | |
|---|---|
| Linker N (50 um) | 2.5 μl |
| LoTE buffer | 27 μl |
| 5 × ligation buffer | 8 μl |

(2) Resuspend, incubate in a water bath at 50° C. for 2 minutes, and then place at room temperature for 10 minutes.
(3) Add 2.5 μl of T4 HC DNA ligase (Invitrogen, 15224-041), resuspend and mix well, place on Thermomixer (Eppendorf) adjusted to a temperature of 16° C. to react for 2 h, and resuspend and mix every 5 minutes during the reaction.
(4) After the reaction, add 600 μl of Wash buffer D, resuspend, place the EP tube on a magnet for 1-2 minutes and then remove the supernatant.
(5) Rewash with 600 μl of Wash buffer D, place the EP tube on a magnet for 1-2 minutes and then remove the supernatant.
(6) Add 600 μl of Wash buffer D, resuspend, transfer the content in the EP tube to a new 1.5 ml EP tube, place the new EP tube on a magnet for 1-2 minutes, remove the supernatant, and resuspend with 200 μl of 1×NEB buffer 4.

Example 8

Digestion with MmeI (1) Place the EP tube on a magnet, carefully remove the 1×NEB buffer 4, and prepare an enzyme digestion system shown in Table 10.

TABLE 10

| | |
|---|---|
| LoTE buffer | 118 μl |
| 10 × NEB buffer 4 | 15 μl |
| 500 μm SAM (S-adenosyl methionine, diluted immediately before use) | 15 μl |
| MmeI | 3 μl |

(2) Place the reaction system on Thermomixer (Eppendorf) for reacting at 37° C. for 70 minutes, resuspend and mix every 10 minutes.
(3) After the reaction has been completed, place the EP tube in a centrifugal machine, and centrifuge at 15000 g for 2 minutes.
(4) Place the EP tube on a magnet for 2 minutes, and collect the supernatant to a new 1.5 ml EP tube.
(5) Successively add 150 μl of LoTE and 300 μl of phenol-chloroform (25:24) to the 1.5 ml EP tube, mix well, place the EP tube in a centrifugal machine and centrifuge at 15000 g for 2 minutes.
(6) Transfer the supernatant to a 2 ml centrifuge tube, successively add 4 μl of glycogen, 200 μl of 7.5M ammonium acetate, and 1.5 ml of pre-cold absolute ethanol, mix well, place the centrifuge tube in a −80° C. refrigerator for 30 minutes, centrifuge at 14000 rpm under 4° C. for 10 minutes, and carefully remove the supernatant by aspiration.

(7) Wash the precipitate in the centrifuge tube with 70% ethanol, place the tube in a centrifugal machine, centrifuge at 14000 rpm under 4° C. for 5 minutes.

(8) Remove the supernatant carefully, dry the precipitate at room temperature for 2 minutes, dissolve the precipitate in 6 µl LoTE.

Example 9

Ligation of Purified MmeI Digested Product to P7 Adaptor

A ligation reaction system containing the precipitated DNA obtained from Example 8 was prepared according to Table 11.

TABLE 11

| DNA | 6 µl |
| P7 adaptor (10 µm) | 1 µl |
| 5 × ligation buffer | 2 µl |
| T4 DNA ligase | 1 µl |

The centrifuge tube containing the ligation reaction system was placed on Thermomixer (Eppendorf) at 16° C. for 3 hours.

Example 10

PCR Amplification

5 µl of the reaction product obtained from Example 9 was used as a template for the PCR amplification, an amplification system was shown in Table 12.

TABLE 12

| DNA ligated with P7 adaptor | 5 µl |
| dNTP (2.5 mM) | 2 µl |
| 5 × Phusion PCR buffer (NEB) | 5 µl |
| Phusion ®high-fidelity DNA polymerase | 1 µl |
| P5 primer (10 µM) | 1 µl |
| P7 primer (10 µM) | 1 µl |
| dH2O | 10 µl |
| TOTAL Volume | 25 µl |

Conditions for the PCR amplification was shown in Table 13.

TABLE 13

| Temperature (° C.) | Time | Number of Cycle |
| --- | --- | --- |
| 98° C. | 2 min | 1 |
| 98° C. | 30 s | |
| 60° C. | 30 s | 9 |
| 72° C. | 5 min | |
| 12° C. | | storing |

Example 11

Extraction and Purification of PCR Products (1) Perform a 6% non-denaturing polyacrylamide gel electrophoresis for the PCR products at 180V for 30 minutes.

(2) Cut out a band in the size of approximately 86-90 bp, place the target band in a 0.5 ml centrifuge tube sleeved with a 2 ml centrifuge tube (wherein the 0.5 ml centrifuge tube was pierced to from six holes at the bottom thereof), and centrifuge at 14000 rpm for 2 minutes to make the band crushed in the 2 ml centrifuge tube.

(3) Add 100 µl of 1×NEB buffer2 into the 2 ml centrifuge tube, place the centrifuge tube on a vertical mixer, and rotate for 2 hours at room temperature.

(4) Transfer all the gel particles and liquid in the centrifuge tube into Spin-X Cellulose Acetate Filter, centrifuge at 14000 rpm for 2 minutes, successively add 1 µl of glycogen, 10 µl of 3M sodium acetate, and 325 µl of pre-cold absolute ethanol in a collecting tube, mix, and store at −80° C. for 30 minutes.

Place the collecting tube in a centrifugal machine, centrifuge at 14000 rpm under 4° C. for 10 minutes, and carefully remove the supernatant.

Wash the precipitate with 70% ethanol, place the tube in a centrifuge machine, centrifuge at 14000 rpm under 4° C. for 5 minutes, and carefully remove the supernatant.

Dry the precipitate at room temperature for 2 minutes, then dissolve the precipitate in Elution buffer (QIAGEN).

Example 12

Library Detection

Agilent 2100 Bioanalyzer (Bioanalyzer analysis system, Agilent, Santa Clara, USA) was used to determine library insertion size and molar concentration of a library; Q-PCR was used to accurately quantify the molar concentration of the library.

Three libraries, one library generated from T4-BGT glycosylation and subsequent MspI digestion of h9 genomic DNA, one library generated from direct MspI digestion of h9 genomic DNA and one library generated from direct HpaII digestion of h9 genomic DNA, were detected by Agilent 2100 Bioanalyzer, and the detecting results are as follows.

Figure 2:
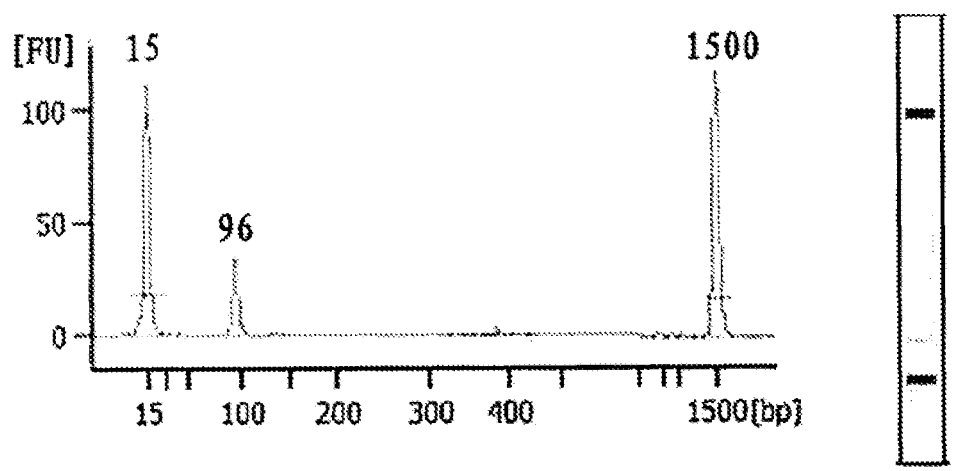
FIG. 2 shows that after PCR amplification, fragments in the three different libraries ligated with Linker N and P7 adaptor at two ends thereof have a size of 96 bp, which is in agreement with a theoretical size.
Figure 2:
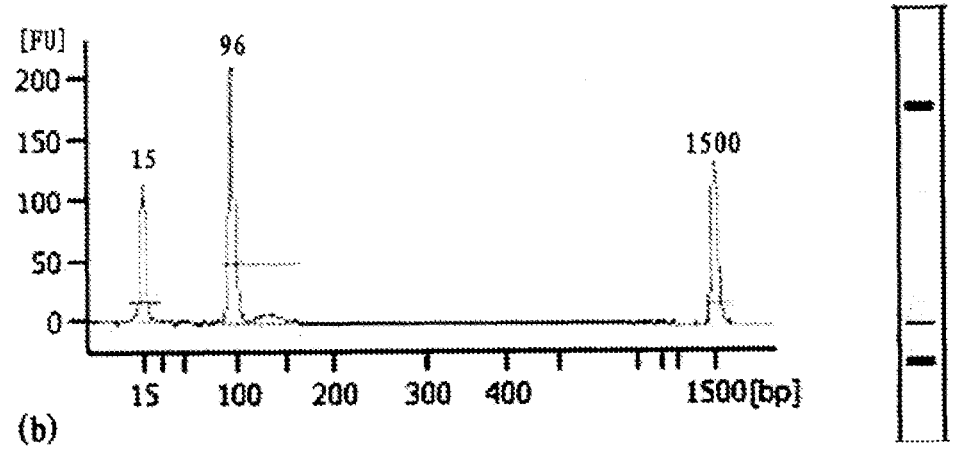
Figure 2:
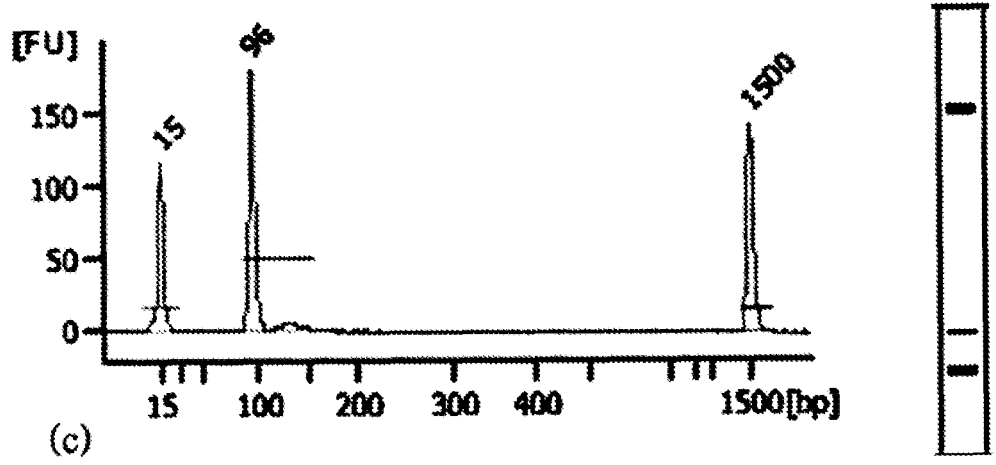

FIG. 2 shows that after PCR amplification and the detection, fragments in the three different libraries, which ligate to Linker N and P7 adaptor at two ends thereof, are all with a fragment size of 96 bp, which is in agreement with a theoretical size; FIG. 2(a) shows a size distribution of the fragments in the library generated from T4-BGT glycosylation and subsequent MspI digestion of h9 genomic DNA; FIG. 2(b) shows a size distribution of the fragments in the library generated from direct MspI digestion of h9 genomic DNA; and FIG. 2(c) shows a size distribution of the fragments in the library generated from direct HpaII digestion of h9 genomic DNA.

Example 13

Sequencing and Data Analysis

After testing, the qualified library was sequenced on HiSeq 2000 sequencer with single-end reads of 50 bp. The sequencing data was normalized, the amount of 20 bp short sequence DNA corresponding to each CCGG site was compared among the three different libraries, and thereby obtaining the information about methylation level and the hydroxymethylation level of each CCGG site. Detailed procedures are as follows:

(1) After testing, the qualified library was sequenced on HiSeq 2000 sequencer with single-end reads of 50 bp.

(2) After sequencing, raw reads from the library was obtained, the sequences of the sequencing adaptor were clipped according to the sequence information of the sequencing adaptor; meanwhile, the raw reads were subjected to a low-quality filtering procedure to remove low-quality raw reads by using the following filtering steps: removing reads which have N base number occupying more than 10% of total base number, and removing reads in which the number of bases having quality value lower than 20 is more than 10% of total base number.

(3) An in-silico digestion of human genome hg19 sequence was performed based on the experiment scheme of the above experiments, then a virtual library consisting of theoretical digestion fragments was produced. An alignment of the filtered reads with the DNA sequences generated by the virtual library was performed with no mismatch allowed. A statistical analysis was performed after the alignment.

(4) After the alignment, the reads in each of the three libraries were pretreated to obtain the sequencing depths of CCGG sites in each of the three libraries, and the sequencing depth data was normalized, based on the following normalization method:

(a) rank the sequencing depths of CCGG sites in each column, i.e., each library, so as to obtain a ranking index of each CCGG site in each library; (b) calculate a square deviation of three ranking indexes for each CCGG site among the three libraries, eliminate a site having a higher square deviation, the amount of the site to be eliminated being equal to (total sites-5000)/4; as for the remaining sites, further rank the sequencing depths of CCGG sites in each column to obtain the ranking index of each CCGG site in each library, calculate the square deviation of three ranking indexes for each CCGG site among the three libraries, eliminate a site having a higher square deviation, the amount of the site to be eliminated being equal to (total sites-5000)/4; the rest were done in the same manner and a total of 4 cycles were performed; the final remaining 5000 sites were used as a baseline for the normalization; and (c) normalize the three libraries according to relative scales of the total amount of sequencing depths of the robust 5000 remaining sites, the normalized amount was scaled to that of the library which could detect C, mC and 5hmC.

(5) The methylation level and the hydroxymethylation level of each CCGG site was calculated according to the normalized data.

Figure 3:
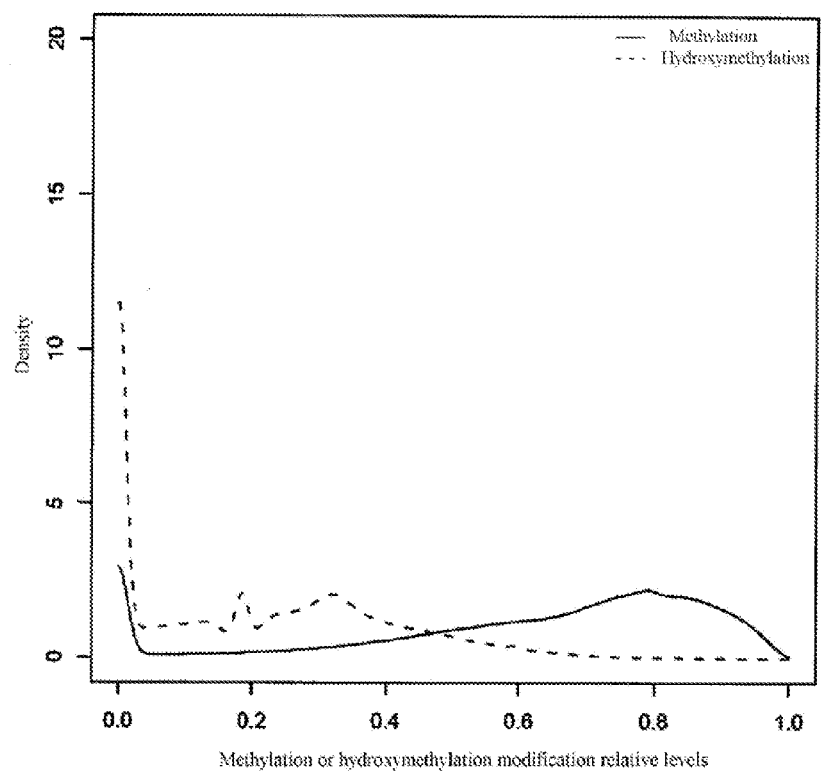
FIG. 3 shows the methylation and hydroxymethylation profiles of all CCGG sites in the sample, wherein the horizontal axis represents modification level, and the vertical axis represents the density of the amount of a certain modified CCGG sites comparing with all amount of CCGG sites, under an indicated specified modification level.
Figure 4:
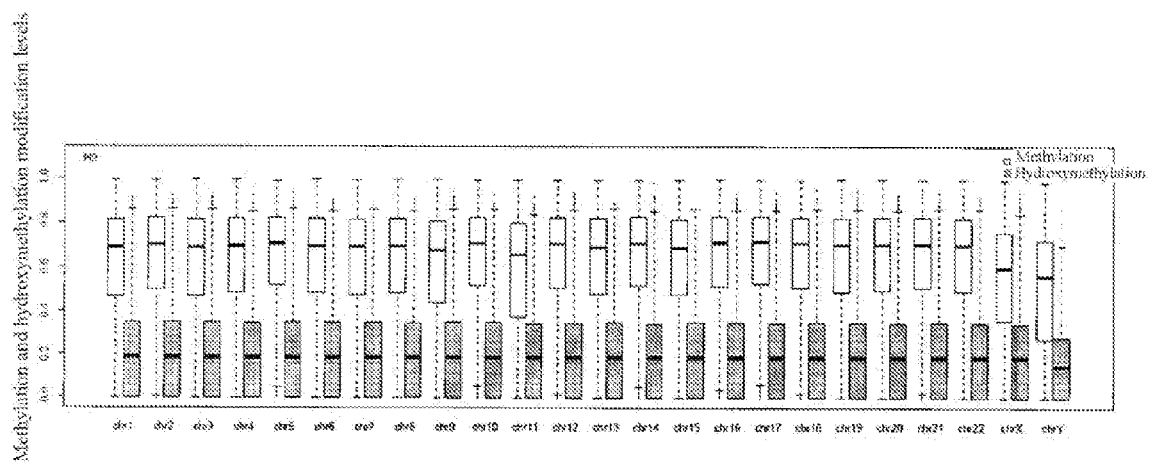
FIG. 4 shows the methylation and hydroxymethylation levels of detected CCGG sites in each chromatin.

(6) Using Perl programming language and R drawing language, and according to the modification information of each CCGG site, overall distributions of methylation and hydroxymethylation levels in the sample and that in different chromatins were calculated by performing statistical analyses, the results were shown in FIG. 3 and FIG. 4.

FIG. 3 shows the methylation and hydroxymethylation profiles of all CCGG sites in the sample, wherein the horizontal axis represents modification level, and the vertical axis represents the density of the amount of a certain modified CCGG sites comparing with all amount of CCGG sites, under an indicated specified modification level. FIG. 3 indicates that the method of the present invention detects two patterns of methylation modification, i.e., low modification level and high modification level for the methylation, but only low modification level for the hydroxymethylation.

FIG. 4 shows an analysis result of methylation and hydroxymethylation modification level in each chromatin. The methylation modification level of each chromatin ranges between 60 and 80%, and mostly around 70%, which is consistent with the existing evidence that methylation level of human genome CG sites is about 70%. At the same time, the inventor of the present invention found that hydroxymethylation modification level of human stem cell h9 is relatively low, which is lower than 20%, this result is also consistent with existing research result that the hydroxymethylation modification level is low. Therefore, the detection method of the present invention is very reliable.

In order to test the accuracy of the method of this invention in detecting methylation modification, the inventor downloaded a published genome bisulfite sequencing data of h9 cell, and the inventor compared the bisulfite sequencing data with the sequencing data obtained by using the enzyme-digestion dependent methylation/hydroxymethylation method of the present invention.

Figure 5:
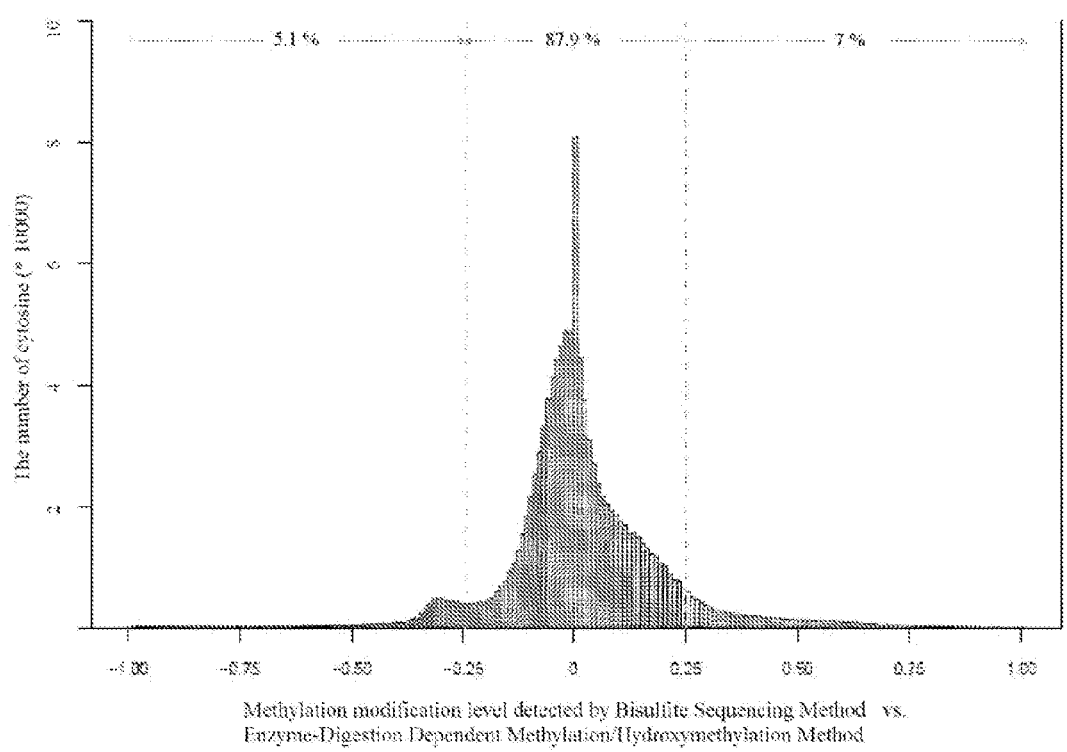
FIG. 5 shows a result of a consistency comparison of data from two methods, i.e., the methylation/hydroxymethylation modification detection method of the present invention and a bisulfite sequencing analysis method.

FIG. 5 shows a result of a consistency comparison of data from two methods, i.e., the methylation/hydroxymethylation modification detection method of the present invention and the bisulfite sequencing analysis method. 87.9% of the methylation modification sites are consistent between the two detection results within ±0.25 level of variance, which is a high consistency. As for the small portion of sites that beyond this range (−0.25, 0.25), it might be resulted from the efficiency of bisulfite conversion, differences in cell status, enzyme-digestion efficiency and so on, but this variance is acceptable, and would not affect the practical application of the method of the present invention.

Example 14

Kit

The present invention further provides a kit for accurately detecting hydroxymethylation modification in nucleic acid samples, comprising the following components:

(1) a first container and a reagent therein for 5hmC glycosylation modification;

(2) a second container and a reagent therein for restriction endonuclease digestion; wherein an dependent unit is provided in the second container, and restriction endonucleases MspI, HpaII, MmeI or Ecop15I, and NlaIII are respectively contained in the dependent unit;

(3) a third container and a biotin-labeled linker therein;

(4) a fourth container and a second linker therein, wherein sequences of the second linker are SEQ ID NO: 3 and SEQ ID NO: 4;

(5) a fifth container, and P5 and P7 adaptors therein;

(6) a sixth container and a reagent used for magnetic bead-based capturing therein;

(7) a seventh container and a reagent used for nucleic acid purification therein; and (8) a specification.

Discussion

NEW ENGLAND BIOLABS, INC. (NEB) has developed a strategy for high-throughput detecting genome-wide hydroxymethylation modification in CCGG sites, and the detailed strategies are as follows:

In step 1, genomic DNA (containing mC and/or hmC) is digested with MspI with 100% digestion efficiency, thus all CCGG sites in the genome, including methylated sites and hydroxymethylated sites are cleaved.

In step 2, digested fragments are treated with Klenow fragment in the presence of dCTP, creating a one base 5'-C overhang.

In step 3, DNA fragments having a size between 40-300 bp, which have been repaired by Klenow fragment, are separated on a 4% agarose gel.

In step 4, the separated DNA is ligated to a double-stranded DNA adapter that has termini with 5'-G overhangs (the adaptor will be used for starting the subsequent amplification and sequencing).

In step 5, purified fragments ligated to the adaptor are glycosylated with BGT, 5 gmC will be created if hydroxymethylation modification exists in CCGG sites in the genomic DNA.

In step 6, the glycosylated products are digested with MspI again, in this step, the adaptor can't be cleaved if the MspI sites are hmC-modified in the genomic DNA sample.

In step 7, one-third of the resulting products are then subjected to PCR amplification and sequence analysis, only molecules in which the adaptors are still attached to both strands will be amplified and sequenced by this process; the remaining two-thirds of the sample are reacted with Klenow fragment and dCTP, the dCTP-filled DNA is ligated with a second double-stranded adapter, which also recreates the MspI site due to the presence of a 5' G overhang and a flanking GC base pair; half of this sample is PCR-amplified and sequenced; the remaining sample is treated with HpaII, then treated with Klenow exo-in the presence of dCTP and ligated to a third adaptor pair, this is then sequenced. Therefore, three groups of amplification products will be detected: the first group of detected sequence has $C^{hm}CGG$ at both ends, the second group of detected sequence has $C^{hm}CGG$ at one end and $C^mGG$ at the other end, and the third group of detected sequence has $C^{hm}CGG$ at one end and CCGG at the other end.

Though a big improvement in 5hmC genome-wide detection is achieved by NEB, there still exists some problems. In the NEB's strategy, dCTP is used during end-repairing processes, for those DNA having hydroxymethylation modification at both strands, only one strand will reserve the hydroxymethylation modification during the end-repairing process, thereby greatly influencing the subsequent enzyme-digestion and generating lots of false modification information. In addition, DNA fragments for detection is selected by gel-cutting (40-300 bp), so the modification information beyond these fragments is not achievable, in other words, the detected sites in this strategy is not complete, and the obtained hydroxymethylation modification information is less than the actual situation.

According to the principle that restriction endonuclease MspI can digest 5mC and 5C, but not glycosylated 5hmC, The inventor of the present invention invents a new and creative strategy for accurately detecting 5hmC at single base resolution. The strategy of the present invention comprises the following steps: designing a biotin-labeled linker, designing a linker having a recognition site of restriction endonuclease MmeI, glycosylating a genomic nucleic acid, digesting with MspI, ligating to the biotin-labeled linker, digesting with NlaIII, capturing with streptavidin magnetic beads, ligating to the linker having the recognition site MmeI, digesting with MmeI, constructing sequencing libraries, sequencing the libraries by high-throughput sequencer, and finally accurately detecting genome-wide hydroxymethylation modification profiles.

All references cited here are incorporated by reference in its entirety for all purposes. The foregoing descriptions are merely specific embodiments of the present invention, but are not intended to limit the protection scope of the present invention. Any variation or replacement readily figured out by persons skilled in the art within the technical scope disclosed in the present invention shall all fall within the protection scope of the present invention.

What is claimed is:

1. A method for detecting hydroxymethylation modification in a nucleic acid in a sample, comprising:
   (1) glycosylating the nucleic acid in the sample to obtain a sample nucleic acid having glycosylated hydroxymethylated bases derived from hydroxymethylated bases present on the nucleic acid in the sample;
   (2) respectively digesting a control nucleic acid that is unglycosylated and the sample nucleic acid obtained from the step (1) by using a first restriction endonuclease to produce first control nucleic acid fragments and sample nucleic acid fragments; digesting the control nucleic acid or the sample nucleic acid by using a second restriction endonuclease to produce second control nucleic acid fragments;
   (3) respectively ligating the first control nucleic acid fragments, the sample nucleic acid fragments and the second control nucleic acid fragments that are obtained from the step (2) to a biotin-labeled linker to produce a first control ligated product, a sample ligated product and a second control ligated product with each ligated product having the biotin-labeled linker;
   (4) respectively digesting the first control ligated product, the sample ligated product and the second control ligated product that are obtained from the step (3) with a NlaIII restriction endonuclease to produce a first control NlaIII digested product, a sample NlaIII digested product and a second control NlaIII digested product, with each NlaIII digested product having the biotin-labeled linker at one end and a sticky end at the other end;
   (5) respectively ligating the first control NlaIII digested product, the sample NlaIII digested product and the second control NlaIII digested product that are obtained from the step (4) to a second linker having a recognition site of a specific restriction endonuclease; then obtaining a first control secondary-ligated product, a sample secondary-ligated product and a second control secondary-ligated product;
   (6) respectively digesting the first control secondary-ligated product, the sample secondary-ligated product and the second control secondary-ligated product that are obtained from the step (5) with the specific restriction endonuclease to produce a first control final digested product, a sample final digested product and a second control final digested product, with each final digested product having the second linker at one end and a sticky end at the other end;
   (7) ligating the first control final digested product, the sample final digested product and the second control final digested product that are obtained from the step (6) to a sequencing adaptor, then amplifying the sequencing adaptor-ligated products to produce a first control sequencing library, a sample sequencing library and a second control sequencing library; and
   (8) sequencing all the libraries obtained from the step (7), analyzing and comparing sequence information to obtain information about hydroxymethylation modification in the nucleic acid;

wherein the nucleic acid in the step (1) is genomic DNA;
   the first restriction endonuclease used in the step (2) is a MspI restriction endonuclease;
   the second restriction endonuclease used in the step (2) is a HpaII restriction endonuclease;
   wherein the glycosylation treatment in the step (1) is achieved by transferring a glucose moiety from a substrate uridine diphosphoglucose to 5-hydroxymethylcytosine (5-hmC) with an enzyme T4-BGT, thereby generating β-glucosyl-5-hydroxymethylcytosine (5-gmC);
   wherein the specific restriction endonuclease used in the step (6) is a MmeI or Ecop15I endonuclease.

2. The method as claimed in claim 1, characterized in that, the biotin-labeled linker used in the step (3) is composed of two paired oligonucleotides, and sequences of the two oligonucleotides are SEQ ID NO: 1 and SEQ ID NO: 2.

3. The method as claimed in claim 1, characterized in that, the step (4) further comprises a step of: capturing fragments produced from the NlaIII digestion by using streptavidin magnetic beads to obtain the first control NlaIII digested product, the sample NlaIII digested product and the second control NlaIII digested product.

4. The method as claimed in claim 1, characterized in that, the second linker used in the step (5) is composed of two paired oligonucleotides, and sequences of the two oligonucleotides are SEQ ID NO: 3 and SEQ ID NO: 4.

5. The method as claimed in claim 1, characterized in that, the second linker used in the step (5) is composed of two paired oligonucleotides, and sequences of the two oligonucleotides are SEQ ID NO: 5 and SEQ ID NO: 6.

6. The method as claimed in claim 1, characterized in that, the second linker used in the step (5) is composed of two paired oligonucleotides, and sequences of the two oligonucleotides are SEQ ID NO: 7 and SEQ ID NO: 8.

7. The method as claimed in claim 1, characterized in that, the specific restriction endonuclease used in the step (6) is MmeI, and the obtained digested products with a length of 20 bp have the second linker at one end and the sticky end at the other end.

8. The method as claimed in claim 1, characterized in that, the specific restriction endonuclease used in the step (6) is Ecop15I, and the obtained digested products with a length of 25 bp have the second linker at one end and the sticky end at the other end.

9. The method as claimed in claim 1, characterized in that, the sequencing adaptor used in the step (7) is composed of two paired oligonucleotides, and sequences of the two oligonucleotides are SEQ ID NO: 9 and SEQ ID NO: 10.

10. The method as claimed in claim 1, characterized in that, the analysis and comparison of sequence information in the step (8) comprise the following steps of:
    (i) filtering raw reads of each library after sequencing to obtain high-quality reads; performing an in-silico digestion of a reference sequence to produce a virtual library consisting of theoretical digested fragments;

(ii) performing an alignment of the high-quality reads with DNA sequences from the virtual library that are both obtained from the step (i); normalizing statistical data produced from the alignment to obtain normalized data of sequencing depths from the three libraries;

(iii) calculating both methylation level and hydroxymethylation level of each CCGG site according to the normalized data obtained from the step (ii); and (iv) performing statistical analyses on the methylation and hydroxymethylation profiles of all CCGG sites in the sample and on the distributions of methylation and hydroxymethylation levels in different chromatins, based on the methylation level and the hydroxymethylation level of each CCGG site obtained from the step (iii).

11. The method as claimed in claim 10, characterized in that, the filtering step in the step (i) comprises:
 (a) removing sequence information of the sequencing adaptor from the raw reads of the library; and/or
 (b) removing reads that have N base number occupying more than 10% of total base number from the raw reads of the library; and/or
 (c) removing reads in which the number of bases having quality value lower than 20 is more than 10% of total base number from the raw reads of the library.

12. The method as claimed in claim 10, characterized in that, the reference sequence in the step (i) is human genome hg18 sequence or hg19 sequence.

13. The method as claimed in claim 10, characterized in that, the normalization in the step (ii) comprises the steps of:
 (A) ranking the sequencing depths of CCGG sites in each library to obtain a ranking index of each CCGG site in each library;
 (B) obtaining a ranking index of each CCGG site in each column, calculating a square deviation of three ranking indexes for each CCGG site, eliminating a site having a higher square deviation by cycling the ranking for n times, using the rest of m sites as a baseline for the normalization, wherein both m and n are positive integers; and
 (C) normalizing the three libraries according to relative scales of the total amount of sequencing depths of the robust m remaining sites.

14. The method as claimed in claim 13, characterized in that, m ranges from 5000 to 15000, and n≥4.

15. A kit for accurately detecting hydroxymethylation modification in genome, comprising the following components:
 (1) a first container and a reagent therein for glycosylation modification;
 (2) a second container and a reagent therein for restriction endonuclease digestion;
 (3) a third container and a biotin-labeled linker therein, wherein the biotin-labeled linker is composed of two paired oligonucleotides, and sequences of the two oligonucleotides are SEQ ID NO: 1 and SEQ ID NO: 2;
 (4) a fourth container and a second linker therein, wherein the second linker is composed of two paired oligonucleotides, and sequences of the two oligonucleotides are SEQ ID NO: 3 and SEQ ID NO: 4; or alternatively, the sequences of the two oligonucleotides are SEQ ID NO: 5 and SEQ ID NO: 6; or alternatively, the sequences of the two oligonucleotides are SEQ ID NO: 7 and SEQ ID NO: 8;
 (5) a fifth container and a sequencing adaptor therein, wherein the sequencing adaptor is composed of two paired oligonucleotides, and sequences of the two oligonucleotides are SEQ ID NO: 9 and SEQ ID NO: 10;
the restriction endonuclease in the second container comprises a MspI, HpaII, MmeI and NlaIII, restriction endonuclease or the restriction endonuclease in the second container comprises a MspI, HpaII, Ecop15I and NlaIII restriction endonuclease;
wherein the reagent for glycosylation modification in the first container comprises substrate uridine diphosphoglucose and enzyme T4-BGT.

\* \* \* \* \*

SEQUENCE LISTING

```
<160> NUMBER OF SEQ ID NOS: 12

<210> SEQ ID NO 1
<211> LENGTH: 30
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: biotinylated
<220> FEATURE:
<221> NAME/KEY: misc_feature
<222> LOCATION: (1)..(30)
<223> OTHER INFORMATION: Biotin-linker

<400> SEQUENCE: 1
tttgcagagg ttcgtaatcg agttgggtgg                                  30

<210> SEQ ID NO 2
<211> LENGTH: 29
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(29)
<223> OTHER INFORMATION: Biotin-linker

<400> SEQUENCE: 2
cgccacccaa ctcgattacg aacctctgc                                   29
```

<210> SEQ ID NO 3
<211> LENGTH: 30
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(30)
<223> OTHER INFORMATION: Linker N

<400> SEQUENCE: 3
acaggttcag agttctacag tccraccatg                               30

<210> SEQ ID NO 4
<211> LENGTH: 22
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: Linker N

<400> SEQUENCE: 4
gtyggactgt agaactctga ac                                       22

<210> SEQ ID NO 5
<211> LENGTH: 35
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(35)
<223> OTHER INFORMATION: Linker N

<400> SEQUENCE: 5
acaggttcag agttctacag tccgacagca gcatg                         35

<210> SEQ ID NO 6
<211> LENGTH: 27
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(27)
<223> OTHER INFORMATION: Linker N

<400> SEQUENCE: 6
ctgctgtcgg actgtagaac tctgaac                                  27

<210> SEQ ID NO 7
<211> LENGTH: 30
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(30)
<223> OTHER INFORMATION: Linker N

<400> SEQUENCE: 7
acaggttcag agttctacag cagcagcatg                                30

<210> SEQ ID NO 8
<211> LENGTH: 22
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: Linker N

<400> SEQUENCE: 8
ctgctgctgt agaactctga ac                                        22

<210> SEQ ID NO 9
<211> LENGTH: 21
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(21)
<223> OTHER INFORMATION: P7 adaptor

<400> SEQUENCE: 9
tcgtatgccg tcttctgctt g                                         21

<210> SEQ ID NO 10
<211> LENGTH: 23
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(23)
<223> OTHER INFORMATION: P7 adaptor
<220> FEATURE:
<221> NAME/KEY: misc_feature
<222> LOCATION: (22)..(23)
<223> OTHER INFORMATION: n is a, c, g, or t

<400> SEQUENCE: 10
caagcagaag acggcatacg ann                                       23

<210> SEQ ID NO 11
<211> LENGTH: 44
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(44)
<223> OTHER INFORMATION: P5 primer

<400> SEQUENCE: 11
aatgatacgg cgaccaccga caggttcaga gttctacagt ccga                44

<210> SEQ ID NO 12
<211> LENGTH: 21
<212> TYPE: DNA
<213> ORGANISM: Artificial sequence
<220> FEATURE:
<223> OTHER INFORMATION: Synthetic
<220> FEATURE:
<221> NAME/KEY: misc_feature

```
<222> LOCATION: (1)..(21)
<223> OTHER INFORMATION: P7 primer

<400> SEQUENCE: 12
caagcagaag acggcatacg a                                              21
```